United States Patent [19]
Benson et al.

[11] Patent Number: 5,643,893
[45] Date of Patent: Jul. 1, 1997

[54] N-SUBSTITUTED-(DIHYDROXYBORYL) ALKYL PURINE, INDOLE AND PYRIMIDINE DERIVATIVES, USEFUL AS INHIBITORS OF INFLAMMATORY CYTOKINES

[75] Inventors: Bradley J. Benson, Chapel Hill, N.C.; Xiannong Chen, Athens, Ga.; George J. Cianciolo, Chapel Hill, N.C.; Jose-Luis Diaz, Durham, N.C.; Khalid S. Ishaq, Chapel Hill, N.C.; Susan L. Morris-Natschke, Apex, N.C.; Ronald J. Uhing, Durham, N.C.; Henry Wong, Morrisville, N.C.

[73] Assignees: Macronex, Inc., Wayne, Pa.; University of North Carolina, Chapel Hill, N.C.

[21] Appl. No.: 264,039

[22] Filed: Jun. 22, 1994

[51] Int. Cl.$^6$ .............. A61K 31/69; C07F 5/02; C07F 5/04

[52] U.S. Cl. .............. 514/64; 544/229; 548/405; 562/7

[58] Field of Search ............... 544/229; 514/64

[56] References Cited

U.S. PATENT DOCUMENTS

| | | | |
|---|---|---|---|
| 4,199,574 | 4/1980 | Schaeffer | 514/81 |
| 5,130,302 | 7/1992 | Spielvogel et al. | 514/45 |
| 5,306,722 | 4/1994 | Kim et al. | 514/274 |
| 5,306,732 | 4/1994 | Norris et al. | 514/729 |

FOREIGN PATENT DOCUMENTS

WO 94/01413  1/1994  WIPO.

OTHER PUBLICATIONS

Ruddle et al., 1990, "An antibody to lymphotoxin and tumor necrosis factor prevents transfer of experimental allergic encephalomyelitis" J. Exp. Med. 172:1193–1200.

Sood et al., 1992, "The synthesis and antineoplastic activity of 2'—deoxynucleoside–cyanoboranes in murine and human culture cells" Anticancer Research 12:335–44.

Sood et al., 1990, "Boron–containing nucleic acids. 2. Synthesis of oligonucleoside boranophosphaates" J. Am. Chem. Soc. 112:9000–1.

Sood et al., 1989, "Boron–containing nucleic acids. 2. Synthesis of cyanoborane adducts of 2'deoxy–nucleosides" J. Am. Chem. Soc. 111:9234–5.

Spielvogel et al., 1991, "From boron analogues of amino acids to boronated DNA: potential new pharmaceuticals and neutron capture agents" Pure & Appl. Chem. 63:415–8.

*Primary Examiner*—Emily Bernhardt
*Attorney, Agent, or Firm*—Klauber & Jackson

[57] ABSTRACT

Novel N-substituted-(dihydroxyboryl)alkyl purine, indole and pyrimidine derivatives have been found to be useful as inhibitors of inflammatory cytokines. They can be used, inter alia, in the therapy of septic shock, cachexia, rheumatoid arthritis, inflammatory bowel disease, multiple sclerosis and AIDS. The compounds are typically prepared by reaction of an bromoalkyl boronic acid with the purine, indole or pyrimidine base.

16 Claims, No Drawings

N-SUBSTITUTED-(DIHYDROXYBORYL) ALKYL PURINE, INDOLE AND PYRIMIDINE DERIVATIVES, USEFUL AS INHIBITORS OF INFLAMMATORY CYTOKINES

BACKGROUND OF THE INVENTION

Tumor necrosis factor alpha (TNF-α), also known as cachectin, is a 17 kDa protein produced by neutrophils, activated lymphocytes, macrophages, NK cells, LAK cells, astrocytes, endothelial cells, smooth muscle cells, and some transformed cells. A large number of studies reveal that TNF-α is produced principally by macrophages and that it may be produced in vitro as well as in vivo. This cytokine mediates a wide variety of biological activities, including: cytotoxic effects against tumor cells, activation of neutrophils, growth proliferation of normal cells, and immunoinflammatory, immunoregulatory, and antiviral responses. TNF-α also induces the secretion of interleukin-1 (IL-1) and is a primary mediator of inflammation and endotoxin-induced shock. A 26 kDa membrane form of TNF-α has been described on the surface of monocytes and activated T cells. This molecule may be involved in intracellular communication, as well as cytotoxic activity, and is a surface marker for lymphocyte activation. By a variety of techniques TNF has been shown to exist as a trimer in aqueous solutions; only a small fraction of human TNF molecules occur as monomers at physiological ionic pH.

Two distinct TNF-α receptors have been identified: a 75 kDa receptor and a 55 kDa receptor, TNFR-α and TNFR-β respectively. The intracellular domains of the two TNF receptor types are apparently unrelated, suggesting that they employ different signal transduction pathways. While both receptors are capable of binding TNF and activating the transcription factor NFkB, it appears that the expression of each receptor is independently and differentially regulated. Human TNF-α will bind to both types of receptors with equal affinity on human cells.

TNF has been found to be an important mediator of the pathophysiological effects of a diverse array of invasive diseases, infections, and inflammatory states. As a consequence of its production (or overproduction) in tissues, and the presence of other cytokines in the cellular environment, TNF may ultimately benefit or injure the host. For instance, when produced acutely and released in large quantities into the circulation during a serious bacterial infection, it triggers a state of shock and tissue injury (septic shock syndrome) that carries an extremely high mortality rate (30 to 90%). Three main lines of evidence indicates that TNF plays a central role in the development of septic shock: (1) administration of the cytokine to mammals induces a state of shock and tissue injury that is nearly indistinguishable from septic shock; (2) inhibiting TNF in septic shock prevents the development of both shock and tissue injury and confers a significant survival advantage; and (3) TNF is produced in animals and humans during experimental and clinical septic shock syndrome.

When produced during chronic disease states, TNF mediates cachexia, a syndrome characterized by anorexia, accelerated catabolism, weight loss, anemia, and depletion of body tissues. Weight loss frequently develops during chronic illness and, if not reversed, may kill the host before the underlying disease can be eradicated. For instance, it is not unusual for the patient afflicted with cancer of AIDS to lose 50% of body weight and to succumb to complications of malnutrition. By contrast to starvation, during which protein-conserving adaptive responses are maximally operative, the cachectic host tends to catabolize body energy stores in the face of suppressed intake, thus hastening its own demise.

In addition to septic shock and cachexia, TNF has been implicated in the pathophysiology of rheumatoid arthritis (RA), inflammatory bowel disease (IBD), multiple sclerosis (MS) and AIDS and has been suggested to perhaps play a role in the development of Alzheimer's disease (AD) and/or the weight loss associated with AD patients.

In rheumatoid arthritis, for instance, there is evidence of macrophage activation with demonstration of increased amounts of two monokines, TNF-α and IL-1, in the serum but even more in the synovial fluid. TNF-α, an inducer of IL-1, is significantly elevated in rheumatoid arthritis but not in reactive arthritis. Moreover, TNF-α levels in RA correlate with the synovial fluid leukocyte count and with the ESR (erythrocyte sedimentation rate). TNF is an important mediator of immunity and inflammation and because of its biologic activities (activation of neutrophils, release of arachidonic acid metabolites from synovial cells, induction of cartilage resorption and inhibition of proteoglycan release in cartilage, induction of macrophase chemotactic activating protein ([MCAP]) is one of the potential mediators in chronic arthritis. Studies have shown that monoclonal antibody to TNF can ameliorate joint disease in murine collagen-induced arthritis. In these studies, anti-TNF administered prior to the onset of disease significantly reduced paw swelling and histological severity of arthritis without reducing the incidence of arthritis or the level of circulating anti-type II collagen IgG. More relevant to human disease was the ability of the antibody to reduce the clinical score, paw swelling, and the histological severity of disease even when injected after the onset of clinical arthritis.

More recently, 20 patients with active rheumatoid arthritis were treated with 20 mg/kg of chimeric human/mouse monoclonal anti-TNF-α in an open phase I/II trial lasting eight weeks. The treatment was well-tolerated and significant improvements were seen in the Ritchie Articular Index, the swollen joint count, and in other major clinical assessments. Significant decreases were seen in serum amyloid A, IL-6 and c-reactive protein.

Multiple sclerosis (MS) is a chronic, inflammatory, demyelinating disease of the central nervous system (CNS). The majority of infiltrating cells at the site of demyelination are macrophages and T-cells. IL-1 and TNF in the CSF are detected at higher levels and more frequently in patients with active multiple sclerosis than in patients with inactive MS or with other neurological diseases. In a study of MS patients, Beck and colleagues found an increase of TNF and interferon production by peripheral blood mononuclear cells two weeks prior to disease exacerbation. Experimental allergic encephalomyelitis (EAE) is the best characterized demyelinating disease of the CNS in animals. EAE and MS share many characteristics. Ruddle and colleagues used a monoclonal antibody which neutralizes TNF to treat EAE in mice. See Ruddle et al., *J. Exp. Med.*, 1990, 172:1193–1200. The incidence and severity of EAE in the antibody-treated mice were dramatically reduced and the onset of disease was delayed. Moreover, the authors reported that the preventive therapy was long-lived, extending through five months of observation.

TNF-α levels were measured in serum samples from 73 HIV-1 seropositive patients and in samples from two control groups. All clinical groups of HIV-1-infected patients, regardless of concurrent illness, had significantly elevated levels of both types of soluble TNF receptors (sTNFRs) and immunoreactive TNF-α, with the highest concentrations among the AIDS patients. These TNF parameters were significantly correlated with reduced CD4+ lymphocyte counts. The raised levels of immunoreactive TNF and sTNFRs strongly indicate activation of the TNF-α system during HIV-1 infection. Levels increase with disease progression and degree of immunodeficiency. Thalidomide, a selective inhibitor of TNF-α synthesis, has been shown to suppress the activation of latent HIV-1 in a monocytoid (U1) cell line. Associated with HIV-1 inhibition was a reduction in agonist-induced TNF-α protein and mRNA production. The presence of thalidomide was also shown to inhibit the activation of virus in the peripheral blood mononuclear cells of 16 out of 17 patients with advanced HIV-1 infection and AIDS. A recent study used reverse transcriptase-polymerase chain reaction on homogenized brain tissue to correlate the relative expression of mRNA for TNF-α with cognitive impairment and with neuropathologic changes in HIV infected patients. Levels of mRNA for TNF-α from frontal subcortical white matter were significantly greater in patients with HIVD (HIV associated dementia) than in AIDS patients without dementia or in seronegative controls. Elevated levels of mRNA for TNF-α in HIVD indicate that abnormal cytokine expression may contribute to the pathogenesis of HIVD. Pentoxifylline (PTX), a drug known to block TNF-α release, was tested in a phase I/II clinical trial of HIV-seropositive patients either alone or in combination with zidovudine (ZDV). The mean HIV-1 viral load, as measured by a quantitative polymerase chain reaction technique, was 1.9-fold above baseline values after 12 weeks of PTX and ZDV compared with 8- to 9-fold greater levels in patients given either agent alone (p<0.05). TNF-α levels correlated with viral load (p<0.0001) in patients given the combined drug regimen.

Crohn's disease and ulcerative colitis are chronic inflammatory bowel diseases of unknown etiology but there is circumstantial evidence that immune mechanisms. play an important role in the pathogenesis of the intestinal lesion and that cytokines produced by lymphoid cells may be critical for the extraintestinal sequelae of the disease. In both Crohn's disease and ulcerative colitis, activation of macrophages seems to be a key feature and increased production of the macrophage-derived cytokines TNF-α, IL-1, and IL-6 have been reported in both diseases. A recent study determined the location and tissue density of cells immunoreactive for TNF-α in intestinal specimens from 24 patients with chronic inflammatory bowel disease (15 with Crohn's, 9 with ulcerative colitis) and 11 controls (14). There was significantly increased density of TNF-α immunoreactive cells in the lamina propria of both ulcerative colitis and Crohn's disease specimens suggesting that this degree of TNF-α production probably contributes significantly to the pathogenesis of both Crohn's disease and ulcerative colitis by impairing the integrity of epithelial and endothelial membranes, increasing inflammatory cell recruitment, and by prothrombotic effects on the vascular endothelium.

SUMMARY OF THE INVENTION

The present invention relates to novel N-substituted-(dihydroxyboryl)alkyl purine, indole and pyrimidine derivatives which are useful as inhibitors of inflammatory cytokines such as IL-lb, IL-6, IL-8, TNFα and tissue factor. More particularly, the present invention relates to novel inhibitors of inflammatory cytokines which are compounds of the Formula I

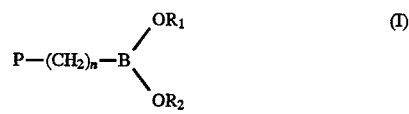

wherein $R_1$ and $R_2$ are both hydrogen atoms or together are a propylene chain bridging the two oxygen atoms;

n is 2–6; and

P is a purine, indole or pyrimidine base residue bonded via the $N^9$ in the case of a purine base, or via the $N^1$ in the case of an indole or pyrimidine base;

and the pharmaceutically acceptable salts thereof.

It is thus an object of the present invention to provide N-substituted-(dihydroxyboryl)alkyl purine, indole and pyrimidine derivatives which, by virtue of their ability to inhibit inflammatory cytokines, are useful as therapeutic agents for the treatment of invasive diseases, infections and inflammatory states, particularly septic shock, cachexia, rheumatoid arthritis, inflammatory bowel disease, multiple sclerosis, AIDS and Alzheimer's disease.

It is further an object of the present invention to provide synthetic procedures for the preparation of the novel N-substituted-(dihydroxyboryl)alkyl purine, indole and pyrimidine derivatives.

It is a still further object of the present invention to provide a method for treating a mammal affected with septic shock, cachexia, rheumatoid arthritis, inflammatory bowel disease and multiple sclerosis which comprises the administration of an agent which is an inhibitor of inflammatory cytokines, namely an N-substituted-(dihydroxyboryl)alkyl purine, an N-substituted-(dihydroxyboryl)alkyl indole or an N-substituted-(dihydroxyboryl)alkyl pyrimidine.

It is thus a further object of the present invention to provide an AIDS therapy which, in addition to decreasing cachexia, decreases viral load, by administration of an N-substituted-(dihydroxyboryl)alkyl purine, indole or pyrimidine which inhibits inflammatory cytokines.

It is a still further object of the present invention to provide a therapeutic agent, namely an N-substituted-(dihydroxyboryl)alkyl purine, indole or pyrimidine which inhibits the development of cachexia by inhibiting TNF and other inflammatory cytokines which are mediators of this disease.

Yet another aspect of the present invention provides a pharmaceutical formulation comprising a compound of Formula I and one or more pharmaceutically acceptable carriers, excipients or diluents.

DETAILED DESCRIPTION OF THE INVENTION

In the pyrimidine base structure the conventional numbering of the substituents is as shown below:

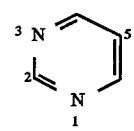

The pyrimidine base portion of the compounds of formula I is bonded to the remainder of the structure through the nitrogen atom at the one-position ($N^1$).

In the purine base structure the conventional numbering of the substituents is as shown below:

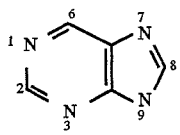

The purine base portion of the compounds of formula I is bonded to the remainder of the structure through the nitrogen atom at the nine-position ($N^9$).

Likewise, in the indole base structure the conventional numbering of the substituents is as shown below:

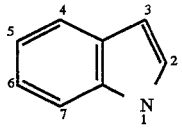

The indole base portion of the compounds of formula I is bonded to the remainder of the structure through the nitrogen atom (the one-position).

In the compounds of Formula I, the pyrimidine, purine or indole base residue can be derived from the naturally occurring pyrimidine bases, i.e., uracil, thymine, or cytosine, the naturally occurring purine bases, adenine and guanine, or commercially available indole bases. The term "purine, indole or pyrimidine bases" refers to these bases, as well as purine and pyrimidine, and analogs thereof, such as derivatives comprising alkyl, aralkyl, halogen, acetyl, hydroxymethyl, amido, and/or carbamate substituents. Accordingly, the dihydroxyboryl bases of the invention may be derived from a naturally occurring base, such as adenine, thymine, cytosine, guanine, uracil, xanthine, or hypoxanthine (the latter two being natural degradation products), indole or from various chemically synthesized analogs thereof known in the art.

Certain illustrative 6- and 2,6-disubstituted purine derivatives are those described as starting materials for the final products described in U.S. Pat. No. 4,199,574, the disclosure of which is incorporated by reference. These purines have the formula

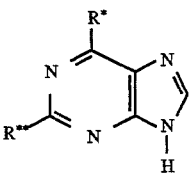

wherein R* is hydrogen, halogen, hydroxy, alkoxy, azide, thio, alkylthio, amino, alkylamino or dialkylamino; and R** is hydrogen, halogen, alkylthio, acylamino, amino or azide. In this formula, halogen includes fluorine, chlorine, bromine and iodine, alkyl groups contain 1–6 carbon atoms and acyl groups contain 2–7 carbon atoms.

Other useful purine and pyrimidine bases are those described in Volumes I–III of "Nucleic Acid Chemistry," ed. by Leroy B. Townsend and R. Stuart Gibson, Wiley Interscience.

In the practice of the instant invention, preferred purine or pyrimidine bases are selected from the group consisting of cytosine, thymine, uracil, 6-chloropurine, 2-amino-6-chloropurine, adenine, guanine, xanthine and hypoxanthine. Of these, 2-amino-6-chloropurine is a highly preferred purine base for use in preparing compounds of the instant invention.

In Formula I, the group —($CH_2$)—$_n$ wherein n is an integer from 2 to 6, represents an alkylene group of 2 to 6 carbon atoms. Representatives of such groups are ethyl, propyl, butyl, pentyl, hexyl, and their corresponding branched chained isomers.

Thus, preferred compounds of formula I are the dihydroxyboryl-purine, indole or pyrimidine derivatives wherein the pyrimidine base portion is derived from cytosine, thymine, uracil, the purine base portion is derived from 6-chloropurine, 2-amino-6-chloropurine, adenine, guanine, xanthine or hypoxanthine, or the indole base portion is derived from indole.

Equivalent to the compounds of Formula I are the biocompatible and pharmaceutically acceptable salts thereof.

The novel compounds of Formula I can be produced by the synthetic pathways shown in Schemes I and II below.

In Scheme I, the synthetic process provides for the preparation of the compounds of Formula I wherein $R_1$ and $R_2$ are both hydrogen atoms.

In Scheme II, the synthetic process provides for the preparation of the compounds of Formula I wherein $R_1$ and $R_2$ together are a propylene chain bridging the two oxygen atoms.

Scheme I

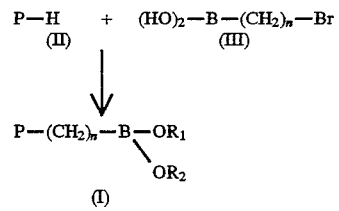

wherein $R_1$ and $R_2$ are both hydrogen atoms and P and n are as hereinabove defined.

In reaction Scheme I, the purine, indole or pyrimidine base of formula II is reacted with the dihydroxyborylalkyl bromide of formula III to afford the compounds of formula I wherein $R_1$ and $R_2$ are both hydrogen atoms, in the presence of a base and an acid acceptor. Typically, the base is an inorganic base, such as potassium carbonate or sodium hydride, with the acid acceptor being potassium carbonate. Reaction times vary from 12 to 48 hours, and usual reaction temperatures are at room temperature.

Scheme II

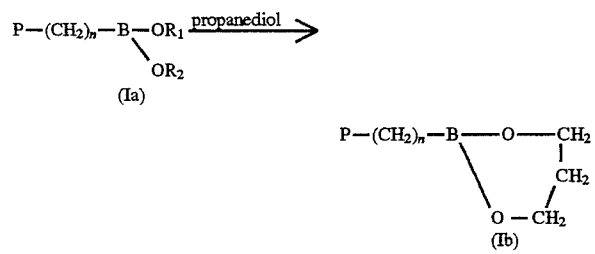

In reaction Scheme II, a compound of formula I wherein both $R_1$ and $R_2$ are hydrogens, and P and n are as hereinbefore defined, is reacted with propanediol in a polar, anhydrous solvent, such as tetrahydrofuran, in order to provide the desired compounds of formula I wherein $R_1$ and $R_2$ are together a propylene chain bridging the two oxygen atoms. Typically, this reaction is conducted for periods of about 4 to 16 hours, and at room temperature.

The starting dihydroxyboryl alkyl bromide of formula III is conveniently prepared by reaction of a gamma-bromo-1- alkene with catecholborane. Typically, this reaction is conducted under a nitrogen atmosphere for a period of time of about 2 to 6 hours and temperatures of about 80° to 100° C., followed by aqueous hydrolysis to obtain the desired product. If desired, this starting dihydroxyboryl alkyl bromide of formula III can be recrystallized from chloroform.

The utility of the compounds of Formula I can be demonstrated by activity in standardized assays, described below.

Unless otherwise described the medium for human cell culture assays is defined as follows: RPMI-1640 is supplemented with 100 U/ml penicillin, 100 µg/ml streptomycin, 2 mM L-glutamine; 1 mM Na pyruvate; 1% MEM nonessential amino acids and 25 mM HEPES; (all from GIBCO, Gaithersburg, Md.). Complete medium is defined as medium supplemented with 5% pooled, heat-inactivated (56° C., 30 minutes) human AB serum (Pel-freeze, Brown Deer, Wis.).

Inhibition of LPS-stimulated Cytokine Production in Whole Blood:

Citrated venous blood was obtained from phlebotomized normal donors and aliquoted into 1 ml volumes in 1.5 ml Eppendorf microcentrifuge tubes (Brinkman Instruments, Westbury, N.Y.). Test compound was prepared by making a 100 mM stock solution in 100% DMSO with all subsequent 1/10 dilutions also made in 100% DMSO. Test compound (1.0 µl) or DMSO alone was then added to 1 ml whole blood so that the final DMSO content was 0.1%. The samples were then rotated at 37° C. for 1 hour whereupon LPS (*S. typhosa*, SIGMA, St. Louis, Mo.) was added to the appropriate samples to a final concentration of 10 ng/ml. All samples were rotated at 37° C. for an additional 14 hours whereupon plasma was harvested by spinning at high speed in a microcentrifuge for 2–3 minutes. Samples were then diluted to 1/25, 1/100 and 1/250 in PBS and assayed by ELISA (R & D Systems, Minneapolis, Minn.) for TNF-$\alpha$, IL-1$\beta$ and IL-6, respectively.

Endotoxin Testing:

All batches of media and reagents are tested to ensure they are free of endotoxins before they are used. This laboratory uses a kinetic chromogenic procedure (Kinetic QCL; Whittaker Bioproducts) for the determination of endotoxin, performed using the Thermomax Plate reader from Molecular Devices. The plate reader incorporates dedicated software for the computer analysis of all data. Samples are tested following the manufacturer's instructions, at 3 different concentrations, in triplicate. Reference Standard Endotoxin (United States Pharmacopeia) obtained at a concentration of 10,000 endotoxin units/ml, is used to generate a standard curve to determine the actual concentration of endotoxin in the samples (sensitivity=/>0.005 endotoxin units/ml).

Human Peripheral Blood Mononuclear Cell (PBMC) Isolation:

Venous blood is obtained from healthy volunteers and mixed with an equal volume of sterile isotonic saline/10 mM HEPES and placed into 50 ml conical polypropylene tubes in 30 ml aliquots. Each aliquot of diluted blood is underlaid with 20–25 ml of sterile Lymphocyte Separation Medium (LSM; Organon-Technika, Durham, N.C.). The tubes are centrifuged at 400 g for 40 minutes at room temperature. The mononuclear cells at the interface are removed and washed twice in sterile isotonic saline/10 mM HEPES followed by a wash in Hank's Balanced Salt Solution (HBSS) or RPMI without serum, depending on their intended use. Cell concentrations for each donor are determined by counting in an haematology analyser (Serono-Baker).

PBMC Proliferation to Mitogens (PHA):

PBMC are adjusted to $4\times10^6$/ml in complete medium. To each well of a 96 well flat bottom tissue culture plate (Falcon 3072) is added 50 µl of cell suspension. Test materials (diluted in complete medium to 2× the desired final concentration) are added in 100 µl volumes to each well. All samples are tested in quadruplicate at four concentrations (spanning 3 $\log_{10}$). Control wells receive complete medium alone. Background response wells receive an additional 50 µl of complete medium, while all other wells receive 50 µl mitogen (diluted in complete medium to 4× the desired final concentration). Dexamethasone (50 µl) at a final concentration of 10 nM is included in each assay as an internal standard for inhibition. The mitogens used and their final concentrations are: OKT3 (anti-CD3 antibody; 100 ng/ml; Ortho) and PHA (phytohaemagglutinin A; 1.0 µg/ml; Sigma). The plates are then incubated for 3 days at 37° C. in humidified 5% $CO_2$, pulsed for the final 6 hours with 0.5 µCi/well of $^3$H-thymidine (6.7 Ci/mmole; Amersham, Arlington Heights, Ill.). in 50 µl complete medium. The contents of the wells are harvested onto glass fibre filters using a multiple automated sample harvester (Tomtec), and the incorporated $^3$H-thymidine determined by liquid scintillation spectrophotometry and represented an cpm (counts per minute) incorporated per well.

Two-Way Mixed Lymphocyte Reaction (MLR):

PBMC are prepared as described for the mitogen assays, but resuspended to $2\times10^6$ cells/ml in complete medium. Fifty µl of cell suspension from two different individuals is then added to each well of a 96-well flat bottom tissue culture plate. An additional 100 µl of complete medium, dexamethasone or test compounds are then added to each well, the plates are incubated for 6 days at 37° C., and then pulsed with $^3$H-thymidine and harvested as previously described.

Monocyte Release of Cytokines and Growth Factors:

Monocytes are prepared by centrifugal counterflow elutriation from peripheral blood mononuclear cells obtained from leukophoresis of normal volunteers (leukopaks) at the Phoresis laboratory located at Duke Hospital, Durham, N.C. We have currently compiled a panel of 24 healthy donors who have been pre-screened and whose peripheral blood mononuclear cells (PBMC) have been found to respond in a normal manner to mitogenic stimulation and stimulation by a specific antigen (tetanus toxoid). Their monocytes have also been found to respond in a normal manner when activated with lipopolysaccharide (LPS) in vitro.

Total cells are taken from leukopaks before elutriation and used to carry out in vitro assays measuring human PBMC responses to mitogens and antigens. PBMC obtained by separation on a LSM gradient (as described above) are resuspended in PBS and separated, using a Beckman elutriator, into lymphocytes and monocytes. Yields of $10^9$ monocytes with greater than 90% purity are routinely obtained.

Purified monocytes prepared as described above are suspended at $4\times10^6$ cells/ml in complete medium. To each well of a 48-well flat bottomed tissue culture plate is added 0.125 ml of cell suspension. Test materials (diluted in complete medium at 2× the desired final concentration) are added in 250 µl volumes to each well. Control wells receive 250 µl of complete medium or 250 µl of IL-4 (diluted to×2 the desired final concentration of 50 ng/ml). All samples are tested at four concentrations in the presence or absence of 100 ng/ml LPS (125 µl of 4× desired final concentration added) and incubated at 37° C. in humidified 5% $CO_2$, for 16 hours. At this time, culture supernatants are aspirated off, and the unattached cells and cell debris are removed by a 2 minute spin in a microcentrifuge at 10,000 g.l The release of cytokines and growth factors is determined in the cell-free supernatants using ELISA capture assays. In this way, testing for IL-1β, TNF-α, IL-1 receptor antagonist, IL-6, IL-8, GM-CSF and PDGF is conducted.

Monocyte Procoagulant Activity (Tissue Factor):

The adhered monocytes remaining on the 48-well tissue culture plates after removal of the supernatants above, are used to measure levels of Tissue Factor production. The cells are solubilized overnight at 4° C. in 10% Triton-×100 in PBS, diluted to 1% Triton-×100 with PBS then assayed by ELISA for Tissue Factor.

Monocyte Release of $PGE_2$, $LTB_4$, and PAF:

Monocytes isolated as described above, were washed and resuspended in RPMl containing 5 mg/ml HSA at $2 \times 10^6$ cells/ml and added to wells of a 48-well plates. The cells were allowed to adhere for 2 hours then washed in HBSS-BSA-HEPES buffer. Test materials were added at four concentrations (175 µl) for 60 minutes; then the monocytes were stimulated by addition of 300 mg/ml zymosan A (175 µl of 2× desired final concentration added). Supernatant medium was collected from the wells after 90 minutes incubation and stored at −20° C. until assayed. Supernatants were assayed for $PGE_2$, $LTB_4$ or PAF using specific scintillation proximity assays (SPA).

Monocyte Superoxide Anion ($O_2$) Release:

Monocytes are prepared as described above and resuspended to $5 \times 10^6$/ml in HBSS containing 10 Mm HEPES, 2 g/l glucose, 0.1% BSA, Ph 7.2. To each well of a 96-well flat bottom, tissue culture plate is added 100 µl of cell suspension and 100 µl of buffer or test materials. Samples are run in quadruplicate. The plate is incubated for 60 minutes at 37° C. followed by the addition of 50 µl of buffer containing cytochrome C (5 mg/ml; type VI, horse heart, Sigma) and bovine liver catalase (1500 U/ml; Sigma) in the presence of zymosan A (ZYM); 750 µg/ml; Sigma). The plate is incubated an additional 120 minutes at 37° C. during which the absorbance at 550 nm is monitored using a microplate reader incorporating dedicated software for kinetic analysis (Molecular Devices; Menlo Park, Calif.).

Inhibition of Monocyte Chemotaxis:

Monocytes are prepared as previously described, and resuspended at $5 \times 10^6$ cells/ml in HBSS, 0.1% BSA (HBSS-BSA). Fluorophore labeling of the cells is carried out by adding calcein-AM to the above cells at a final concentration of 2 µM. Following a 30 minute incubation at 37° C. in humidified 5% $CO_2$, the labeled monocytes are washed twice and incubated in a range of dilutions of the test materials for 60 minutes at 37° C. in humidified 5% $CO_2$. The pre-treated, calcein-AM loaded cells are then added in triplicate to the wells of the top compartment of a Neuro-Probe (Cabin, John, M.D.) 96-well chemotaxis chamber ($2 \times 10^5$ cells/well) and permitted to migrate through a 10 µm thick bonded polycarbonate membrane (5 µm porosity; NeuroProbe Inc; Cabin, John, M.D.) towards the wells of the lower compartment containing the chemoattractant (FMLP) at $5 \times 10^{-9}$ M. After a 90 minute incubation at 37° C. in a humidified chamber, the wells of the upper chambers are aspirated, the monocyte-associated membrane removed, non-migrating cells wiped off and the filters permitted to air dry to 15 minutes. The number of cells migrating through the membranes are quantified by measuring the fluorescent intensity of the migrating cells in a fluorescent microplate reader (CytoFluor 2300, Millipore Corp., Bedford, Mass.)

Monocyte Adherence to Vascular Endothelial Cells:

Human umbilical vein endothelial cells (HUVEC) are obtained from Clonetics (San Diego, Calif.). Confluent layers of epithelial cells are prepared by seeding 96-well plates with $2 \times 10^4$ cells/well and incubating at 37° C. in humidified 5% $CO_2$ for 24 hours. TNFα (50 µg) was then added to each well (10 µl of a 5 ng/ml stock solution) prior to the addition of monocytes. Monocytes are fluorescently labelled and pre-treated with test materials as described above, resuspended in complete medium to a final concentration of $2 \times 10^6$ cells/ml and incubated in triplicate in wells (100 µl/well) for 60 minutes at 37° C. in humidified 5% $CO_2$. Plates are then sealed and centrifuged at 250 g for 5 minutes to remove non-adhered monocytes and the number of adhered cells determined by reading plates on a fluorescent microplate reader.

When tested in the above standardized assays, a representative compound of Formula I, i.e., 2-amino-6-chloro-9-(4-dihydroxyborylbutyl)purine, was found to give the following results shown below in Table 1.

TABLE 1

COMPOUND:
2-amino-6-chloro-9-(4-dihydroxyborylbutyl)purine

| ASSAY | EFFECT | UNITS: µm $EC_{50}$ |
|---|---|---|
| ENDOTOXIN | NE | |
| PHA | INHIB | 100.00 |
| MLR | INHIB | 50.00 |
| GM-CSF | INHIB | 6.8 |
| IL1β | NE | |
| IL1ra | NE | |
| IL6 | NE | |
| IL8 | NE | |
| TNFα | INHIB | 0.57 |
| TISSUE FACTOR | INHIB | 2.10 |
| $PGE_2$ | | |
| $LTB_4$ | INHIB | 90.5 |
| PAF | NE | |
| SUPEROXIDE | NE | |
| CHEMOTAXIS | NE | |
| MTS | TC | 100.00 |
| LDH | TC | 100.00 |

Key:
NE No effect
NT Not tested
INHIB Inhibition
STIM Stimulation
$IC_{40}$ 40% Inhibitory Concentration
$EC_{50}$ 50% Effective Concentration
TC Tolerated Concentration The ability of the compounds of formula I to inhibit the action of various inflammatory cytokines make them useful in a wide variety of therapeutic methods. Specifically, their ability to mediate or inhibit the actions of TNF-a makes these compounds useful in the treatment of various invasive diseases, infections, and inflammatory states. Particularly important is the inhibition of the large amount of TNF produced during serious bacterial infections, which can trigger a state of shock and tissue injury (septic shock syndrome).

A further important use of the compounds of formula I is to inhibit the TNF which is known to mediate cachexia produced during chronic disease states. Thus, these compounds are particularly useful in adjunctive therapy for AIDS and cancer patients to reduce and/or ameliorate the consequences of cachexia produced during these chronic disease states.

A further specific method of treatment for which the compounds of the instant invention are particularly useful is in the treatment of rheumatoid arthritis wherein increased amounts of the inflammatory cytokines, TNF-a and IL-1 are present. By virtue of their ability to mediate and/or inhibit the action of these cytokines, inflammation and the severity of the disease state can be reduced or eliminated.

The compounds of the instant invention can also be utilized in the treatment of multiple sclerosis (MS), Crohn's disease and ulcerative colitis by inhibiting and the activity of the inflammatory cytokines which underlie these disease states.

The compounds of the present invention are likewise useful in the therapeutic methods described in U.S. Pat. No. 5,306,732 by virtue of their ability to act as antagonist of tumor necrosis factor. The compounds for use in the methods of the present invention can be, and are preferably, administered as medicaments, i.e., pharmaceutical compositions.

The pharmaceutical compositions used in the methods of this invention for administration to animals and humans comprise the compounds of Formula I in combination with a pharmaceutical carrier or excipient.

The medicament can be in the form of tablets (including lozenges and granules), dragees, capsules, pills, ampoules or suppositories comprising the compound of the invention.

"Medicament" as used herein means physically discrete coherent portions suitable for medical administration. "Medicament in dosage unit form" as used herein means physically discrete coherent units suitable for medical administration, each containing a daily does or a multiple (up to four times) or a sub-multiple (down to a fortieth) of a daily dose of the active compound of the invention in association with a carrier and/or enclosed within an envelope. Whether the medicament contains a daily dose or, for example, a half, a third or a quarter of a daily dose will depend on whether the medicament is to be administered once or, for example, twice, three times a day, respectively.

Advantageously, the compositions are formulated as dosage units, each unit being adapted to supply a fixed dose of active ingredients. Tablets, coated tablets, capsules, ampoules and suppositories are examples of preferred dosage forms according to the invention. It is only necessary that the active ingredient constitute an effective amount, i.e., such that a suitable effective dosage will be consistent with the dosage form employed in single or multiple unit doses. The exact individual dosages, as well as daily dosages, will, of course, be determined according to standard medical principles under the direction of a physician or veterinarian. The compounds of Formula I can also be administered as suspensions, solutions and emulsions of the active compound in aqueous or non-aqueous diluents, syrups, granulates or powders.

Diluents that can be used in pharmaceutical compositions (e.g., granulates) containing the active compound adapted to be formed into tablets, dragees, capsules and pills include the following: (a) fillers and extenders, e.g., starch, sugars, mannitol and silicic acid; (b) binding agents, e.g., carboxymethyl cellulose and other cellulose derivatives, alginates, gelatine and polyvinyl pyrrolidone; (c) moisturizing agents, e.g., glycerol; (d) disintegrating agents, e.g., agar-agar, calcium carbonate and sodium bicarbonate; (e) agents for retarding dissolution, e.g., paraffin; (f) resorption accelerators, e.g., quaternary ammonium compounds; (g) surface active agents, e.g., cetyl alcohol, glycerol monostearate; (g) adsorptive carriers, e.g., kaolin and bentonite; (i) lubricants, e.g., talc, calcium and magnesium stearate and solid polyethylene glycols.

The tablets, dragees, capsules and pills comprising the active compound can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, from polymeric substances or waxes.

The compounds of Formula I can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g., cocoa oil and high esters, [e.g., $C_{14}$-alcohol with $C_{16}$-fatty acid]) or mixtures of these diluents.

The pharmaceutical compositions which are solutions and emulsions can, for example, contain the customary diluents (with, of course, the above-mentioned exclusion of solvents having a molecular weight below 200, except in the presence of a surface-active agent), such as solvents, dissolving agents and emulsifiers. Specific non-limiting examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example, ground nut oil, glycerol, tetrahydrofurfuryl alcohol, polyethylene glycols and fatty acid esters of sorbitol or mixtures thereof.

For parental administration, solutions and suspensions should be sterile, e.g., water or arachis oil contained in ampoules and, if appropriate, blood-isotonic.

The pharmaceutical compositions which are suspensions can contain the usual diluents, such as liquid diluents, e.g., water, ethyl alcohol, propylene glycol, surface active agents (e.g., ethoxylated isostearyl alcohols, polyoxyethylene sorbitols and sorbitan esters), microcrystalline cellulose, aluminum metahydroxide, bentonite, agar-agar and tragacanth, or mixtures thereof.

The pharmaceutical compositions can also contain coloring agents and preservatives, as well as perfumes and flavoring additions (e.g., peppermint oil and eucalyptus oil), and sweetening agents, (e.g., saccharin and aspartame).

The pharmaceutical compositions will generally contain from 0.5 to 90% of the active ingredient by weight of the total composition.

In addition to the compounds of Formula I, the pharmaceutical compositions and medicaments can also contain other pharmaceutically active compounds.

Any diluent in the medicaments of the present invention may be any of those mentioned above in relation to the pharmaceutical compositions. Such medicaments may include solvents of molecular weight less than 200 as the sole diluent.

It is envisaged that the compounds of Formula I will be administered perorally, parenterally (for example, intramuscularly, intraperitoneally, subcutaneously, transdermally or intravenously,), rectally or locally, preferably orally or parenterally, especially perlingually, or intravenously.

The dosage rate, e.g., 0.05 to 20 mg/kg of body weight, will be a function of the nature and body weight of the human or animal subject to be treated, the individual reaction of this subject to the treatment, type of formulation in which the active ingredient is administered, the mode in which the administration is carried out and the point in the progress of the disease or interval at which it is to be administered. Thus, it may in some case suffice to use less than a minimum dosage rate, while other cases an upper limit must be exceeded to achieve the desired results. Where larger amounts are administered, it may be advisable to divide these into several individual administrations over the course of the day.

The following examples describe in detail compounds and compositions illustrative of the present invention. It will be apparent to those skilled in the art that many modifications, both of materials and methods, may be practiced without departing from the purpose and intent of this disclosure.

EXAMPLES

All melting points were taken on a Thomas Hoover melting point apparatus and are uncorrected. Infrared spectra (IR) were recorded on a Perkin-Elmer 1320 spectrophotometer. $^1$H NMR spectra were obtained using a Bruker AC-300 NMR. The assignment of complex NMR signals was accomplished by comparison with known standard spectra. The chemical shifts were reported in parts per million relative to an internal standard of tetramethylsilane. Elemental analyses were performed by Atlantic Microlab Inc., Norcross, Ga. and electrospray mass spectroscopy was performed by Dr. David Millington, School of Medicine, Duke University, Durham, N.C. Thin layer chromatography (TLC) was performed on 13 inch fluorescent precoated Whatman Silica Gel 60 Å TLC plates. The TLC plates were visualized by UV light, iodine vapor, or charring following sulfuric acid spray. Silica gel (70–230 mesh) from Fisher Scientific was used for column chromatography. Reagents were purchased from Aldrich. Solvents, including acetonitrile, N,N-dimethylformamide (DMF), methylene chloride, and tetrahydrofuran (THF), were dried by placement over molecular sieves (4 Å) for 2 weeks before use.

EXAMPLE A

4-Bromobutyl boronic acid

4-Bromo-1-butene (5.4 g, 40 mmol) was added to catecholborane (5.76 g, 48 mmol). The reaction mixture was stirred under nitrogen and heated to 95° C. for 4 hours. The unreacted starting material was distilled under high vacuum (1 mm Hg) at room temperature. Water (70 mL) was added to the slightly yellow liquid residue and stirred for 2 hours. The white solid was filtered and recrystallized from chloroform. Crystals (5.6 g) were obtained and were used in the next step without further purification. Yield 78%; mp 81°–83° C.; $^1$H NMR (DMSO-d6) 0.58–0.67 (t, B C$\underline{H}$2), 1.40–1.52 (m, B CH2 C$\underline{H}$2), 1.61–1.85 (m, C$\underline{H}$2 CH2 Br), 3.48–3.58 (t, CH2 C$\underline{H}$2 Br), 7.40–7.48 (s, ($\underline{H}$O)2 B).

EXAMPLE 1

1-(4-Dihydroxyborylbutyl)thymine

Potassium carbonate (0.6 g, 4.4 mmol) was added to a solution of thymine (0.56 g, 4.4 mmol) in dimethylformamide (15 mL) and stirred for 30 minutes. To this reaction mixture, 4-bromobutyl boronic acid (0.4 g, 2.2 mmol) dissolved in dimethylformamide (5 mL) was added dropwise, and stirring was continued 2 days at room temperature. After the potassium carbonate was filtered, the dimethylformamide was evaporated under high vacuum. The residue was purified on a silica gel column eluting with a discontinuous gradient of chloroform/methanol (95:5, 85:15). The appropriate TLC-homogenous fractions were pooled and evaporated to give 0.22 g of pure product. Yield 44%; mp 130°–132° C.; $^1$H NMR (DMSO-d6) 0.55–0.68 (t, B C$\underline{H}$2), 1.22–1.35 (m, B CH2 C$\underline{H}$2), 1.42–1.60 (m, B CH2 CH2 C$\underline{H}$2), 1.72–1.78 (s, C$\underline{H}$3 C5 thymine), 3.52–3.63 (CH2 C$\underline{H}$2 N), 7.40–7.43 (s, ($\underline{H}$O)2 B), 7.48–7.51 (s, $\underline{H}$ C6 thymine), 11.12–11.18 (s, $\underline{H}$N thymine). Elemental Analysis (C9H15BO4N2); Calcd. C, 47.82%; H, 6.69%; N, 12.40%; Found C, 47.71%; H, 6.72%; N, 12.35%.

EXAMPLE 2

6-Chloro-9-(4-dihydroxyborylbutyl)purine

Sodium hydride (0.22 g, 7.2 mmol) was added to a solution of 6-chloropurine (0.93 g, 6.0 mmol) in dimethylformamide (20 mL) and stirred for 10 minutes. 4-Bromobutyl boronic acid (1.1 g, 6.0 mmol) in dimethylformamide (5 mL) was added to the reaction mixture and stirred at room temperature for 16 hours. After the removal of the dimethylformamide under high vacuum, the residue was purified by column chromatography (chloroform/methanol discontinuous gradient 95:5, 9:1) to yield 0.78 g of pure product. Yield 51%; mp 135°–138° C.; $^1$H NMR (DMSO-d6) 0.55–0.68 (t, B C$\underline{H}$2), 1.22–1.35 (m, B CH2 C$\underline{H}$2), 1.78–1.91 (m, B CH2 CH2 C$\underline{H}$2), 4.26–4.32 (t, CH2 C$\underline{H}$2 N), 7.40–7.42 (s, ($\underline{H}$O)2 B), 8.68–8.70 (s, $\underline{H}$ C8 purine), 8.80–8.81 (s, $\underline{H}$ C2 purine). Elemental Analysis. (C9H12BO2N4Cl); Calcd. C, 42.47%; H, 4.75%; N, 22.02%; Found C, 42.48%; H, 4.80%; N, 22.06%.

EXAMPLE 3

2-Amino-6-chloro-9-(4-dihydroxyborylbutyl)purine

The title compound was synthesized in a similar manner as the compound of Example 1 with 2-amino-6-chloropurine (1.36 g, 8 mmol), 4-bromobutyl boronic acid (1.45 g, 8 mmol), and potassium carbonate (1.66 g, 12 mmol) in dimethylformamide (20 mL). Yield 56%; Wt. 1.2 g; mp 154°–156° C.; $^1$H NMR (DMSO-d6) 0.55–0.68 (t, B C$\underline{H}$2), 1.20–1.32 (m, B CH2 C$\underline{H}$2), 1.68–1.77 (m, B CH2 CH2 C$\underline{H}$2), 4.00–4.08 (t, CH2 C$\underline{H}$2 N), 6.85–6.92 (s, $\underline{H}$2N C2 purine), 7.40–7.42 (s, ($\underline{H}$O)2 B), 8.10–8.12 (s, $\underline{H}$ C8 purine). Electrospray Mass Spectrum (MH)$^+$ (low resolution); Calcd. 270.09 (C9H13O2N5BCl); Found 270.10 (37 ppm).

EXAMPLE 4

9-(4-Dihydroxyborylbutyl)guanine

The compound prepared in Example 3, 2-amino-6-chloro-9-(4-dihydroxyborylbutyl)purine, (0.5 g, 1.85 mmol) was added to aqueous HCl (5 mL, 2N), and the reaction mixture was heated to reflux for 5 hours. After cooling to room temperature, aqueous NaOH (10%) was added to neutralize the reaction mixture to pH 7. Water was evaporated under high vacuum, and methanol was added to the residue to remove the unreacted starting material. The remaining solid was washed with water (3×20 mL), then stirred in water overnight. After filtration, the product was air-dried for 2 days. Yield 81%; Wt. 0.38 g; mp 202°–205° C.; $^1$H NMR (DMSO-d6) 0.55–0.68 (t, B C$\underline{H}$2), 1.20–1.32 (m, B CH2 C$\underline{H}$2), 1.62–1.75 (m, B CH2 CH2 C$\underline{H}$2), 3.88–3.98 (t, CH2 C$\underline{H}$2 N), 6.33–6.50 (s, $\underline{H}$2N C2 guanine), 7.40–7.45 (s, ( $\underline{H}$O)2 B), 7.68–7.71 (s, $\underline{H}$ C8 guanine), 10.47–10.53 ($\underline{H}$ N3 guanine). Electrospray Mass Spectrum (MH)$^+$ (low resolution); Calcd. 252.12 (C9H14O3N5B); Found 252.10 (79 ppm).

EXAMPLE 5

9-(4-Dihydroxyborylbutyl)hypoxanthine

The title compound was synthesized according to the procedure of Example 4 from 6-chloro-9-(4-dihydroxyborylbutyl)purine (as prepared in Example 2) (88 mg, 0.35 mmol). Yield 82%; Wt. 67 mg; mp 182°–184° C.; $^1$H NMR (DMSO-d6) 0.55–0.68 (t, B C$\underline{H}$2), 1.22–1.35 (m, B CH2 C$\underline{H}$2), 1.70–1.82 (m, B CH2 CH2 C$\underline{H}$2), 4.05–4.16 (t, CH2 C$\underline{H}$2 N), 7.38–7.40 (s, ($\underline{H}$O)2 B), 8.01–8.03 (s, $\underline{H}$ C8 hypoxanthine), 8.04–8.10 (s, $\underline{H}$ C2 hypoxanthine), 12.20–12.30 ($\underline{H}$ N3 hypoxanthine). Electrospray Mass Spectrum (M)$^+$ (low resolution); Calcd. 236.11 (C9H13O3N4B); Found 236.10 (42 ppm).

EXAMPLE 6

6-Chloro-9-[4-(1,3-propyldioxaborylbutyl]purine

6-Chloro-9-(4-dihydroxyborylbutyl)purine (as prepared in Example 2) (70 mg, 0.28 mmol) and 1,3-propanediol (22 mg, 0.28 mmol) were dissolved in tetrahydrofuran (10 mL) and stirred at room temperature overnight. The tetrahydrofuran was evaporated by influx of nitrogen. Hexane and ether (95:5) was used to dissolve the product. The solid residue was discarded and pure product (60 mg) was obtained after the evaporation of the solvents. Yield 74%; Wt. 60 mg; mp 85°–87° C.; $^1$H NMR (DMSO-d6) 0.55–0.68 (t, B CH2), 1.22–1.35 (m, B CH2 CH2), 1.80–1.90 (m, B CH2 CH2 CH2; O CH2 CH2 CH2 O), 3.82–3.95 (m, O CH2 CH2 CH2 O) 4.22–4.36 (t, CH2 CH2 N), 8.68–8.70 (s, H C8 purine), 8.80–8.81 (s, H C2 purine).

EXAMPLE 7

Repetition of the procedure detailed in Example 4 utilizing indole as the starting material affords 1-(4-dihydroxyborylbutyl)indole.

EXAMPLE 8

| Tablet Formulation | |
|---|---|
| Ingredient | mg/tablet |
| Compound of formula I | 50 |
| Starch | 50 |
| Mannitol | 75 |
| Magnesium stearate | 2 |
| Stearic acid | 5 |

The compound of formula I, a portion of the starch and the lactose are combined and wet granulated with starch paste. The wet granulation is placed on trays and allowed to dry overnight at a temperature of 45 degrees Centigrade. The dried granulation is comminuted in a comminutor to a particle size of approximately 20 mesh. Magnesium stearate, stearic acid and the balance of the starch are added and the entire mix blended prior to compression on a suitable tablet press. The tablets are compressed at a weight of 232 mg. using a $^{11}/_{32}$" punch with a hardness of 4 kg.

What is claimed is:

1. A compound of the formula

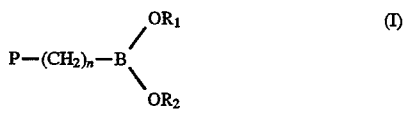

wherein $R_1$ and $R_2$ are both hydrogen atoms, or together are a propylene chain bridging the two oxygen atoms;

n is 2–6; and

P is a purine or pyrimidine base residue selected from the group consisting of thymine, guanine, and hypoxanthine and 6-substituted- or 2,6-disubstitued-purines wherein the substituents are selected from the group consisting of halogen and amino, bonded via the $N^9$ in the case of a purine base or via the $N^1$ in the case of a pyrimidine base; and the pharmaceutically acceptable salts thereof.

2. The compound according to claim 1 wherein $R_1$ and $R_2$ are both hydrogen.

3. The compound according to claim 2 wherein n is 4.

4. The compound according claim 3 wherein the pyrimidine base residue is derived from thymine.

5. The compound according to claim 3 wherein the purine base residue is derived from guanine.

6. The compound according to claim 3 wherein the purine base residue is derived from hypoxanthine.

7. The compound according to claim 3 wherein the purine base residue is derived from 6-chloropurine.

8. A compound of the formula

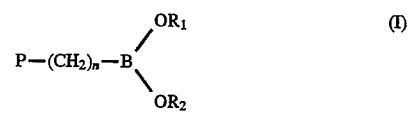

wherein $R_1$ and $R_2$ are both hydrogen atoms; n is 4; and P is a purine base residue bonded via the $N^9$ derived from 2-amino-6-chloropurine.

9. A pharmaceutical composition which comprises a therapeutically effective amount of a compound of the formula

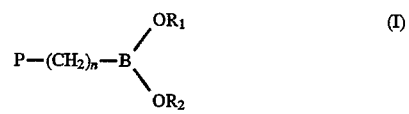

wherein both $R_1$ and $R_2$ are both hydrogen atoms, or together are a propylene chain bridging the two oxygen atoms; n is 2–6; and P is a purine or pyrimidine base residue selected from the group consisting of thymine, guanine, hypoxanthine and 6-substituted- or 2,6-disubstitued-purines wherein the substituents are selected from the group consisting of halogen and amino, bonded via the $N^9$ in the case of a purine base or via the $N^1$ in the case of a pyrimidine base; and a carrier therefor.

10. The composition according to claim 9 wherein $R_1$ and $R_2$ are both hydrogen.

11. The composition according to claim 10 wherein n is 4.

12. The composition according claim 11 wherein the pyrimidine base residue is derived from thymine.

13. The composition according to claim 11 wherein the purine base residue is derived from guanine.

14. The composition according to claim 11 wherein the purine base residue is derived from hypoxanthine.

15. The composition according to claim 11 wherein the purine base residue is derived from 6-chloropurine.

16. A pharmaceutical composition which comprises a therapeutically effective amount of a compound of the formula

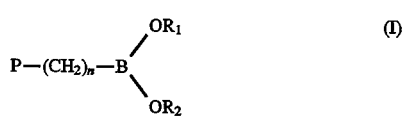

wherein both $R_1$ and $R_2$ are both hydrogen atoms; n is 4; and P is a purine base residue bonded via the $N^9$ derived from 2-amino-6-chloropurine and a carrier therefor.

* * * * *